(12) United States Patent
Collins et al.

(10) Patent No.: US 7,157,478 B2
(45) Date of Patent: Jan. 2, 2007

(54) OXADIAZOLE DERIVATIVES FOR INHIBITION OF GAMMA SECRETASE

(75) Inventors: Ian James Collins, Redhill (GB); Laura Catherine Cooper, Puckeridge (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 269 days.

(21) Appl. No.: 10/511,915

(22) PCT Filed: Apr. 24, 2003

(86) PCT No.: PCT/GB03/01777

§ 371 (c)(1),
(2), (4) Date: Oct. 18, 2004

(87) PCT Pub. No.: WO03/093264

PCT Pub. Date: Nov. 13, 2003

(65) Prior Publication Data

US 2005/0119293 A1   Jun. 2, 2005

(30) Foreign Application Priority Data

May 1, 2002   (GB) .................... 0209995.0

(51) Int. Cl.
*A61K 31/41*   (2006.01)
*C07D 417/00*  (2006.01)

(52) U.S. Cl. ..................... 514/362; 548/134

(58) Field of Classification Search ........... 514/362; 548/134
See application file for complete search history.

(56) References Cited

U.S. PATENT DOCUMENTS 7,041,688 B1 *   5/2006   Campbell et al. ........... 514/362
7,041,689 B1 *   5/2006   Collins et al. .............. 514/362
7,078,424 B1 *   7/2006   Hamilton et al. ........... 514/381

FOREIGN PATENT DOCUMENTS

WO   WO 01/70677   9/2001
WO   WO 02/36555   5/2002

* cited by examiner

*Primary Examiner*—Deborah C. Lambkin
(74) *Attorney, Agent, or Firm*—John C. Todaro; Melvin Winokur

(57) ABSTRACT

Compounds of formula I: wherein X represents a 5-(R-substituted)-1,2,4-oxadiazole-3-yl moiety are inhibitors of gamma-secretase, and hence useful for treating Alzheimer's disease

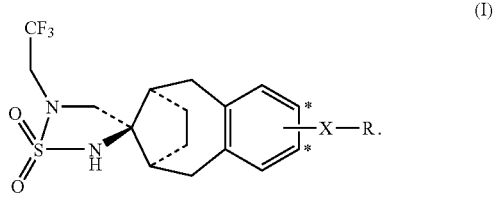

(I)

7 Claims, No Drawings

OXADIAZOLE DERIVATIVES FOR INHIBITION OF GAMMA SECRETASE

CROSS REFERENCE TO RELATED APPLICATIONS

This application is a U.S. National Phase application under 35 U.S.C. § 371 of PCT Application No. PCT/GB03/01777, filed Apr. 24, 2003, which claims priority under 35 U.S.C. § 119 from GB Application No. 0209995.0, filed May 1, 2002.

The present invention relates to a novel class of compounds, their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID *research alert* 1996 1(2): 1–7; ID *research alert* 1997 2(1):1–8; Current Opinion in CPNS Investigational Drugs 1999 1(3):327–332; and Chemistry in Britain, Jan. 2000, 28–31.)

Aβ is a peptide comprising 39–43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its NH$_2$-and COOH-termini. At least two secretory mechanisms exist which release APP from the membrane and generate the soluble, COOH-truncated forms of APP (APP$_s$). Proteases which release APP and its fragments from the membrane are termed "secretases". Most APP$_s$ is released by a putative α-secretase which cleaves within the Aβ domain (between residues Lys$^{16}$ and Leu$^{17}$) to release α-APP$_s$ and precludes the release of intact Aβ. A minor portion of APP$_s$ is released by a β-secretase, which cleaves near the NH$_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

WO 01/70677 discloses certain sulphonamido-substituted bridged bicycloalkyl derivatives which are useful in the treatment of Alzheimer's disease, but neither discloses nor suggests the compounds of the present invention.

The present invention provides a novel class of non-peptidic compounds which are useful in the treatment or prevention of AD by modulating the processing of APP by the putative γ-secretase, thus arresting the production of Aβ and preventing the formation of insoluble plaques.

According to the invention there is provided a compound of formula I:

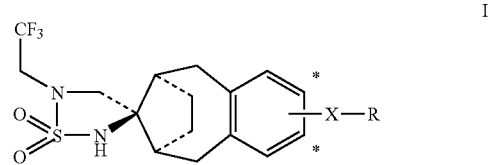

wherein the moiety X—R is attached at one of the positions indicated by an asterisk;

X is a 5-(R-substituted)-1,2,4-oxadiazol-3-yl moiety; and

R is selected from:
  (i) a non-aromatic hydrocarbon group of up to 10 carbon atoms, optionally substituted with halogen, CF$_3$, CHF$_2$, CN, OH, CO$_2$H, C$_{2-6}$acyl, C$_{1-4}$alkoxy or C$_{1-4}$alkoxycarbonyl;
  (ii) a non-aromatic heterocyclic group comprising up to 7 ring atoms of which up to 3 are chosen from N, O and S and the remainder are carbon, bearing 0–3 substituents independently selected from oxo, halogen, CN, C$_{1-6}$alkyl, OH, CF$_3$, CHF$_2$, CH$_2$F, C$_{2-6}$acyl, CO$_2$H, C$_{1-4}$alkoxy and C$_{1-4}$alkoxycarbonyl; and
  (iii) phenyl or 6-membered heteroaryl, either of which bears 0–3 substituents independently selected from halogen, CF$_3$, CHF$_2$, CH$_2$F, NO$_2$, CN, OCF$_3$, C$_{1-6}$alkyl and C$_{1-6}$alkoxy; or a pharmaceutically acceptable salt thereof.

In a preferred embodiment of the invention, R represents a group selected from those set forth under (iii) above.

It will be readily apparent to those skilled in the art that the compounds of formula I exist in two enantiomeric forms, depending on which of the ring positions indicated by an asterisk is bonded to the moiety —X—R. It is to be emphasised that the invention, for each identity of —X—R, encompasses both enantiomers, either as homochiral compounds or as mixtures of enantiomers in any proportion. Furthermore, structural formulae depicting attachment of —X—R or a synthetic precursor thereof at one of the said ring positions shall hereinafter be indicative of attachment at either or both of said ring positions, unless expressly stated otherwise. The homochiral compounds may be named as [6S,9R,11R]2',3',4',5,5',6,7,8,9,10-decahydro-2-(5-(R-substituted)-1,2,4-oxadiazol-3-yl)-5'-(2,2,2-trifluoroethyl)spiro [6,9-methanobenzocyclooctene-11,3'-[1,2,5]thiadiazole]1', 1'-dioxides and [6R,9S,11S]2',3',4',5,5',6,7,8, 9,10-decahydro-2-(5-(R-substituted)-1,2,4-oxadiazol-3-yl)-5'-(2, 2,2-trifluoroethyl)spiro[6,9-methanobenzocyclooctene-11, 3'-[1,2,5]thiadiazole] 1',1'-dioxides. The [6S,9R,11R] isomers are preferred.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 4.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The expression "$C_{3-6}$ cycloalkyl($C_{1-6}$)alkyl" as used herein includes cyclopropylmethyl, cyclobutylmethyl, cyclopentylmethyl and cyclohexylmethyl.

The expression "$C_{2-6}$acyl" as used herein refers to ($C_{1-5}$alkyl)carbonyl groups, such as acetyl, propanoyl and butanoyl, including cycloalkyl derivatives such as cyclopentanecarbonyl and cyclobutanecarbonyl, and fluorinated derivatives such as trifluoroacetyl.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X is a 5-(R-substituted)-1,2,4-oxadiazol-3-yl moiety.

In one embodiment, R is a non-aromatic hydrocarbon group of up to 10 carbon atoms, optionally substituted with halogen, $CF_3$, $CHF_2$, CN, OH, $CO_2H$, $C_{2-6}$acyl, $C_{1-4}$alkoxy or $C_{1-4}$alkoxycarbonyl. Within this definition, R may comprise cyclic or acyclic hydrocarbon residues or combinations thereof, saturated or unsaturated, up to a maximum of 10 carbon atoms in total, and may bear a substituent as detailed above. Within this embodiment, R typically contains up to 6 carbon atoms. Suitable examples include alkyl groups such as methyl, ethyl, n-propyl, isopropyl, n-butyl, sec-butyl, t-butyl and 2-methylpropyl, cycloalkyl groups such as cyclopropyl, cyclobutyl, cyclopentyl and cyclohexyl, cycloalkylalkyl groups such as cyclopropylmethyl and cyclopentylmethyl, alkenyl groups such as allyl, cyclopentenyl and cyclohexenyl, and alkynyl groups such as propargyl.

In a second embodiment, R represents a non-aromatic heterocyclic group comprising up to 7 ring atoms of which up to 3 are chosen from N, O and S and the remainder are carbon, bearing 0–3 substituents independently selected from oxo, halogen, CN, $C_{1-6}$alkyl, OH, $CF_3$, $CHF_2$, $CH_2F$, $C_{2-6}$acyl, $CO_2H$, $C_{1-4}$alkoxy and $C_{1-4}$alkoxycarbonyl. Suitable heterocyclic groups include pyrrolidine, piperidine, tetrahydropyridine, piperazine, morpholine, thiomorpholine, thiomorpholine-1,1-dioxide, pyran and thiopyran. Heterocyclic groups containing one or more nitrogen atoms may be bonded to X via carbon or via nitrogen. Within this embodiment, R very aptly represents 1-acetylpiperidin-4-yl.

In a third embodiment, R represents phenyl or 6-membered heteroaryl, either of which: bears 0–3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by X include pyridyl, pyrazinyl, pyrimidinyl, pyridazinyl and triazinyl. Preferably, the phenyl or heteroaryl ring bears 0 to 2 substituents. Phenyl groups represented by R preferably bear at least one substituent. Preferred substituents include halogen (especially chlorine and fluorine) and $CF_3$. Within this embodiment, examples of groups represented by R include monohalophenyl, dihalophenyl, pyridyl, monohalopyridyl and trifluoromethylpyridyl, wherein "halo" refers to fluoro or chloro. Suitable specific values for R include 2-fluorophenyl, 2-chlorophenyl, 4-fluorophenyl, 4-chlorophenyl, 2,4-difluorophenyl, 2,4-dichlorophenyl, pyridin-2-yl, pyridin-3-yl, pyridin-4-yl, pyrazin-2-yl, 5-fluoropyridin-2-yl, 5-chloropyridin-2-yl, 5-(trifluoromethyl)pyridin-2-yl and 6-(trifluoromethyl)pyridin-3-yl, and preferred examples include 4-fluorophenyl, pyridin-2-yl, pyridin-3-yl, pyridin-4-yl, pyrazin-2-yl, 5-fluoropyridin-2-yl, 5-chloropyridin-2-yl, 5-(trifluoromethyl)pyridin-2-yl, and 6-(trifluoromethyl)pyridin-3-yl.

Representative compounds in accordance with the invention include those in which the moiety —X—R is selected from:

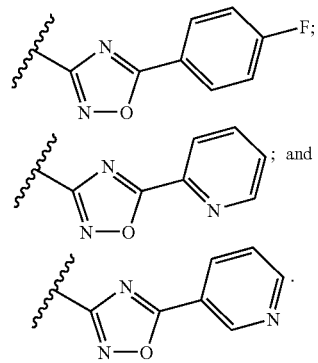

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above-containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

The liquid forms in which the novel compositions of the present invention may be incorporated for administration orally or by injection include aqueous solutions, suitably-flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 50 mg/kg of body weight per day. The compounds may be administered on a regimen of 1 to 4 times per day. In some cases, however, a dosage outside these limits may be used.

The compounds of the invention are particularly suitable for oral administration.

Suitable starting materials for the preparation of the compounds of formula I are the ketones II:

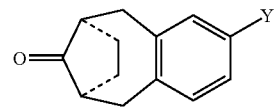

wherein Y represents alkoxycarbonyl (especially $CO_2Me$ or $CO_2Et$) or benzyloxy. Treatment of the ketones II with t-butylsulphonamide in the presence of $TiCl_4$ and triethylamine in refluxing dichloroethane provides the sulphonylimines III(a):

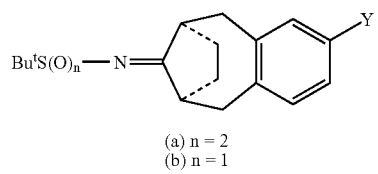

(a) n = 2
(b) n = 1 where Y has the same meaning as before. Alternatively, treatment of the ketones II with t-butylsulphinamide in the presence of $Ti(OEt)_4$ in refluxing tetrahydrofuran provides the sulphinylimines III(b).

Both types of imine III react with trimethylsulphoxonium iodide to provide aziridines IV:

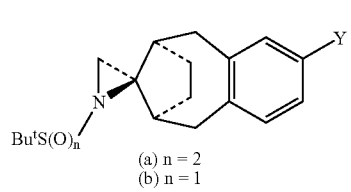

(a) n = 2
(b) n = 1 where Y has the same meaning as before. The reaction takes place in the presence of sodium hydride at ambient temperature in a THF-DMSO mixture or at 0° C. in DMSO.

Reaction of sulphonamides IV(a) with $CF_3CH_2NH_2$, followed by cleavage of the t-butylsulphonyl group, provides diamines V:

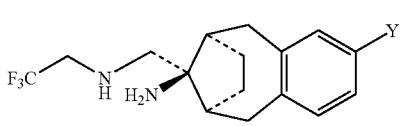

where Y has the same meaning as before. Ring-opening of the aziridine is typically effected by heating with $CF_3CH_2NH_2$ at 100° C. in DMF or DMSO in a sealed tube, while cleavage of the t-butylsulphonyl group may be effected by treatment with trifluoromethanesulphonic acid at 0° C.

Alternatively, the diamines V may be formed directly by reaction of the sulphinamides IV(b) with CF$_3$CH$_2$NH$_2$ in the presence of zinc iodide in dichloroethane at 100° C.

Reaction of diamines V with sulphamide (H$_2$NSO$_2$NH$_2$) in refluxing anhydrous pyridine provides the cyclic sulphamides VI(a) and (b):

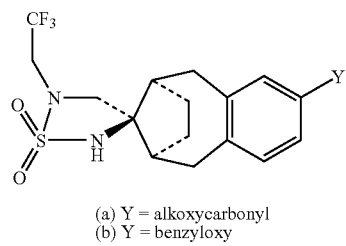

VI (a) Y = alkoxycarbonyl
(b) Y = benzyloxy

Compounds VI(a) and (b) are key intermediates for the preparation of compounds of formula I since the substituent Y may be transformed into the moiety —X—R by various standard synthetic techniques.

Hydrolysis of the esters VI(a) (for example, using sodium hydroxide in aqueous THF at 60° C.) provides the acid VII which serves as the precursor for suitable heteroaryl structures.

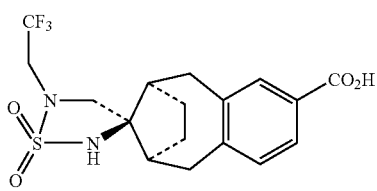

VII

The acid VII may be converted to the corresponding nitrile IX, which also serves as precursor for heteroaryl derivatives in accordance with formula I.

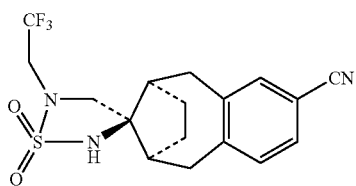

IX

The nitrile is readily formed by first converting the acid to the corresponding carboxamide, then reacting it with triflic anhydride in the presence of triethylamine in dichloromethane at ambient temperature. The amide may be formed by treatment of the acid firstly with pentafluorophenol and dicyclohexylcarbodiimide, and then with ammonia.

The nitrile IX may be converted to the corresponding amidoxime by treatment with hydroxylamine hydrochloride in refluxing ethanolic sodium hydroxide solution. Subsequent coupling with a carboxylic acid RCO$_2$H and cyclisation provides a 1,2,4-oxadiazol-3-yl derivative X:

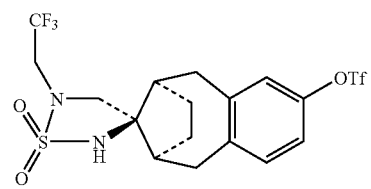

X where R has the same meaning as before. The coupling may be carried out using carbonyldiimidazole in DMF at 70° C., while the final cyclisation may be effected by treatment with toluenesulphonic acid in a refluxing DMF-toluene mixture.

The benzyl ether VI(b) may be converted to the corresponding phenol by hydrogenation over Pd/C, and thence to the triflate XI by treatment with triflic anhydride in the presence of pyridine in dichloromethane at 0° C.:

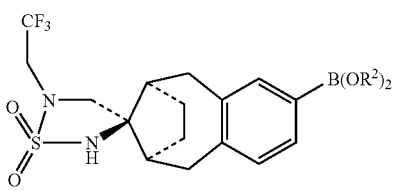

XI where Tf represents triflyl (i.e. trifluoromethanesulphonyl). The triflate XI is another precursor of compounds in accordance with formula I.

Thus, XI may be converted to a boronic acid derivative XII:

XII where R$^2$ represents H or alkyl, or the two OR$^2$ groups complete a cyclic boronate ester such as the pinacolate. The conversion may be achieved by conventional means using a suitable boron reagent, such as bis(pinacolato)diboron, in the presence of a Pd(II) catalyst such as bis(diphenylphosphinoferrocene)dichloropalladium(II), typically in the presence of potassium acetate in DMF at 100° C.

Reaction of boronates XII with R—X—L, where L is a suitable leaving group (such as halogen, especially bromine or iodine) and R and X have the same meanings as before, provides compounds of formula I directly. The reaction takes place in the presence of the same Pd catalyst as used in the preparation of XII.

Alternatively, the R—X moiety may be assembled in a three-stage process in which firstly an HX— group is introduced by reaction of boronate XII with HX—L, where L and X have the same meanings as before; secondly, the resulting product is brominated to convert the HX— group to Br—X—; and thirdly, reaction with R—B(OR$^2$) provides a compound of formula I, where R and R$^2$ have the same meanings as before.

It will be apparent to those skilled in the art that, in many cases, the steps in the synthetic schemes described above may be carried out in a different order. Thus, if desired, the group Y in ketones II may be converted to the moiety R—X— by one of the described routes prior to the construction of the spiro-linked sulphamide ring.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

In a preferred route to enantiomerically pure compounds of formula I, racemic intermediates VI(a) or VI(b) are subjected to preparative chiral HPLC to provide the corresponding homochiral intermediates, which are then converted to homochiral compounds of formula I by the routes indicated above.

Where they are not commercially available, the starting materials and reagents used in the above-described synthetic schemes may be prepared by conventional means. The ketones II may be prepared by the method described in *J. Org. Chem.*, 47, 4329–34, 1987.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.
(2) Cells are placed in 96-well plates at 30,000/well/100 μL in minimal essential medium (MEM) (phenol red-free)+10% foetal bovine serum (FBS), 50 mM HEPES buffer (pH7.3), 1% glutamine, 0.2 mg/ml G418 antibiotic, 10 mM sodium butyrate.
(3) Make dilutions of the compound plate. Dilute stock solution to 5.5% DMSO/110 μM compound. Mix compounds vigorously and store at 4° C. until use.
(4) Add 10 μL compound/well. Mix plate briefly, and leave for 18 h in 37° C. incubator.
(5) Remove 90 μL of culture supernatant and dilute 1:1 with ice-cold 25 mM HEPES (pH0.3), 0.1% BSA, 1.0 mM EDTA (+broad spectrum protease inhibitor cocktail; pre-aliquotted into a 96-well plate). Mix and keep on ice or freeze at −80° C.
(6) Add back 100 μL of warm MEM+10% FBS, 50 mM HEPES (pH7.3), 1% glutamine, 0.2 mg/ml G418, 10 mM sodium butyrate to each well, and return plate to 37° C. incubator.
(7) Prepare reagents necessary to determine amyloid peptide levels, for example by ELISA assay.
(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.
(9) Quantitate amyloid beta 40 and 42 peptides using an appropriate volume of diluted culture medium by standard ELISA techniques.
(10) Add 15 μL/well MTS/PES solution to the cells; mix and leave at 37° C.
(11) Read plate when the absorbance values are approximately 1.0 (mix briefly before reading to disperse the reduced formazan product).

Alternative assays are described in *Biochemistry*, 2000, 39(30), 8698–8704.

The compounds of the present invention show unexpectedly high affinities as measured by the above assays. Thus the following Examples all had an $ED_{50}$ of less than 50 nM, typically less than 10 nM, and frequently about 1 nM in at least one of the above assays. In general, the compounds also exhibit good oral-bioavailability and/or brain penetration, and are largely free from undesirable biological interactions with potential to cause toxic side effects.

The following examples illustrate the present invention.

EXAMPLES

Intermediate A

[6S/R,9R/S,11R/S]2',3',4',5,5',6,7,8,9,10-Decahydro-2-carboxy-5'-(2,2,2-trifluoroethyl)-spiro[6,9-methanobenzocyclooctene-11,3'-[1,2,5]thiadiazole]1',1'-dioxide

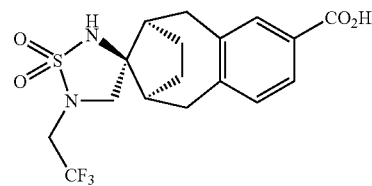

Step 1: Methyl 11-Oxo-5,6,7,8,9,10-hexahydro-6,9-methanobenzocyclooctene-2-carboxylate

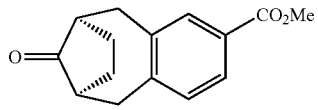

Prepared using the procedure described for 11-oxo-5,6,7,8,9,10-hexahydro -6,9-methanobenzocyclooctene (Justus Liebigs Ann. Chem. 1961, 650, 115) using methyl 3,4-bis (bromomethyl)benzoate in place of 1,2-bis(bromomethyl) benzene.

Step 2: Methyl 11-(2'-Methyl-propane-2'-sulfonylimino)-5,6,7,8,9,10-hexahydro-6,9-methanobenzocyclooctene-2-carboxylate

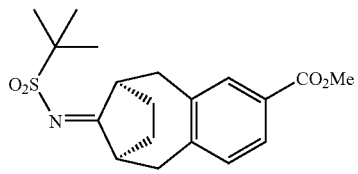

A solution of titanium (I) chloride (25 mL, 1M in DCM) was added at r.t. to a stirred suspension of the ketone from Step 1 (10.0 g), tert-butyl sulfonamide (5.8 g) and triethylamine (11.6 mL) in 1,2-dichloroethane (100 mL). The yellow suspension was stirred under nitrogen for 30 minutes, then refluxed for 8 hours. The mixture was diluted with dichloromethane (400 mL) and saturated aqueous sodium hydrogencarbonate (400 mL) and filtered through a pad of Celite. The organic phase was dried ($Na_2SO_4$), filtered and concentrated to give the sulfonimine (15.5 g, quantitative) as a brown gum. δ ($^1H$, 360 MHz, $CDCl_3$) 1.20–1.40 (2H, m), 1.50 (9H, s), 1.75–2.00 (2H, m), 2.90–2.95 (2H, m), 3.05–3,20 (3H, m), 3.92 (3H, s), 3.95–4.05 (1H, m), 7.24–7.28 (1H, m), 7.84–7.87 (2H, m).

Step 3: Methyl [6S/R,9R/S,11R/S]-11-[(2'-Methyl-propane-2'-sulfonyl)-1'-aza-spiro[2,4]]-5,6,7,8,9,10-hexahydro-6,9-methanobenzocyclooctene-2-carboxylate

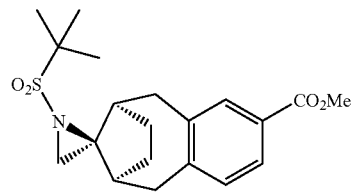

Sodium hydride (55%, 1.75 g) was added portionwise at room temperature to a stirred suspension of trimethylsulfoxonium iodide (8.8 g) in DMSO (70 mL) under nitrogen. After stirring for 2 hours, the solution was cooled in an ice-bath and a solution of the sulfonimine from Step 2 (10.0 g) in DMSO (80 mL) was added. The mixture was stirred at room temperature for 2.5 hours then poured onto ice (500 mL) and diluted with water (200 mL). The white solids were collected, rinsed with diethyl ether and dried under vacuum at room temperature to give the aziridine (8.16 g, 79%). MS (ES+) 400 ([MNa]$^+$).

Step 4: Methyl [6S/R,9R/S,11S]-11-(2'-Methyl-propane-2'-sulfonylamino)-11-(2,2,2-trifluoroethyl)aminomethyl-5,6,7,8,9,10-hexahydro-6,9-methanobenzocyclooctene-2-carboxylate

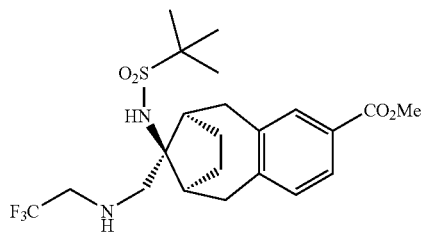

A solution of the aziridine from Step 3 (8.16 g) and 2,2,2-trifluoroethylamine (10.2 mL) in DMSO (45 mL) was divided into 3 equal portions and stirred at 100° C. in sealed tubes for 6 days. The cooled solutions were combined and poured into water (250 mL). The white crystalline solid was collected, rinsed with diethyl ether and dried under vacuum at room temperature to give the amine (7.43 g, 72%). MS (ES+) 477 ([MH]$^+$).

Step 5: Methyl [6S/R,9R/S,11R/S]11-Amino-11-(2,2,2-trifluoroethyl)aminomethyl-5,6,7,8,9,10-hexahydro-6,9-methanobenzocyclooctene-2-carboxylate

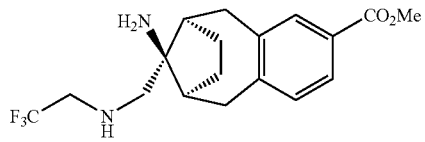

Trifluoromethanesulfonic acid (11 mL) was added dropwise at 0° C. to a stirred suspension of the sulfonamide from Step 4 (7.43 g) in dichloromethane (100 mL) under nitrogen. The mixture was stirred at 0° C. for 20 minutes, then at room temperature for 4 hours. The mixture was poured into saturated aqueous sodium hydrogencarbonate (600 mL) and extracted with 10% methanol-dichloromethane (2×300 mL). The extracts were washed with brine (100 mL), dried over $Na_2SO_4$, filtered and concentrated to give the diamine (6.5 g, quantitative) as a yellow oil. MS (ES+) 357 ([MH]$^+$).

Step 6: [6S/R,9R/S,11R/S]2',3',4',5,5',6,7,8,9,10-Decahydro-2-carbomethoxy-5'-(2,2,2-trifluoroethyl)-spiro[6,9-methanobenzocyclooctene -11,3'-[1,2,5] thiadiazole]1',1'-dioxide

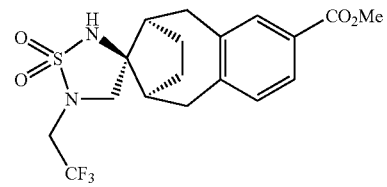

A solution of the diamine from Step 5 (6.5 g) and sulfamide (4.5 g) was reluxed in pyridine (120 mL) for 6 hours. Solvent was removed by evaporation. The residue was partitioned between 1M HCl (200 mL) and 10% methanol-dichloromethane (500 mL). The organic extract was washed with brine (100 mL), dried over Na$_2$SO$_4$, filtered and concentrated. The solid was rinsed with diethyl ether to give the cyclic sulfamide (5.26 g, 80%) as an off-white powder. δ ($^1$H 360 MHz, CDCl$_3$) 1.26–1.30 (2H, m), 1.70–1.75 (2H, m), 2.47–2.50 (2H, m), 2.74–2.82 (2H, m), 3.21–3.29 (2H, m), 3.41–3.47 (2H, m), 3.68 (2H, q, J=9), 3.90 (3H, s), 4.78 (1H, s), 7.17 (1H, d, J=8), 7.78–7.80 (2H, m)

Step 7: [6S/R,9R/S,11R/S]2',3',4',5,5',6,7,8,9,10-Decahydro-2-carboxy-5'-(2,2,2-trifluoroethyl)-spiro[6,9-methanobenzocyclooctene-11,3'-[1,2,5]thiadiazole]1',1'-dioxide

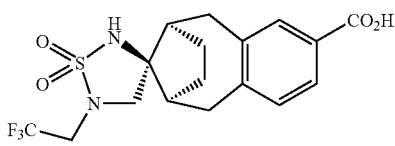

A mixture of 4M sodium hydroxide (3 mL) and the ester from Step 6 (2.33 g) in tetrahydrofuran (30 mL) was stirred at 60° C. for 3.5 hours. The mixture was diluted with 1M citric acid (10 mL) and 1M hydrochloric acid (20 mL) and extracted with dichloromethane (2×100 mL). The extracts were washed with water (100 mL), brine (100 mL), dried over Na$_2$SO$_4$, filtered and concentrated. Trituration with diethyl ether—isohexane gave the acid (1.96 g, 88%) as an off-white solid. δ ($^1$H, 360 MHz, d$_6$-DMSO) 0.95–1.05 (2H, m), 1.65–1.75 (2H, m), 2.35–2.42 (2H, m), 2.62–2.72 (2H, m), 3.18–3.23 (2H, m), 3.47 (2H, s), 4.02 (2H, q, J=10), 7.23 (1H, d, J=8), 7.62–7.70 (2H m), 8.03 (1H, s), 12.60 (1H, s).

Example 1

[6S/R,9R/S,11R/S]-2',3',4',5,5',6,7,8,9,10-Decahydro-2-(5-(4-fluorophenyl)-1,2,4-oxadiazol-3-yl)-5'-(2,2,2-trifluoroethyl)spiro[6,9-methanobenzocyclooctene-11,3'-[1,2,5]thiadiazole]1',1'-dioxide Step 1: [6S/R,9R/S,11R/S]-2',3',4',5,5',6,7,8,9,10-Decahydro-2-amidoxime-5'-(2,2,2trifluoroethyl)spiro[6,9-methanobenzocyclooctene-11,3-[1,2,5]thiadiazole]1',1'-dioxide

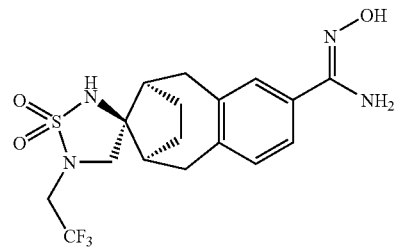

Pentafluorophenol (0.341 g, 1.85 mmol) and N,N'-dicyclohexylcarbodiimide (0.382 g, 1.85 mmol) were added to a suspension of Intermediate A (0.5 g, 1.24 mmol) in ethyl acetate (30 mL) and the reaction was stirred at room temperature for 1 hour after which time it was homogeneous. The solvent was removed in vacuo. Ethyl acetate was added to the residue and the resulting white solid removed by filtration. The filtrate was evaporated in vacuo. The residue was dissolved in dichloromethane (50 ml) and ammonia gas was bubbled through until the mixture was cloudy. The reaction was stirred for 1 hour at room temperature. The solvent was removed in vacuo and the residue purified by flash column chromatography on silica, eluting with 20% ethyl acetate-isohexane followed by 5% methanol-dichloromethane, to give the carboxamide (0.385 g, 77%).

A solution of this (0.2 g, 0.5 mmol) and (methoxycarbonylsulfamoyl)triethyl-ammonium hydroxide, inner salt, (0.177 g, 1.74 mmol) in tetrahydrofuran (10 mL) was heated under reflux for 4 hours. The solvent was removed in vacuo and the residue purified by flash column chromatography on silica, eluting with 25% ethyl acetate-isohexane, to give the nitrile (0.115 g, 60%).

A solution of this (0.1 g, 0.26 mmol), hydroxylamine hydrochloride (0.027 g, 0.39 mmol) and triethylamine (65 µL, 0.47 mmol) in ethanol (5 mL) was heated under reflux for 18 hours. The cooled reaction mixture was poured into sodium hydroxide solution (1M aq; 25 mL) and extracted with ethyl acetate (25 mL). The organic layer was washed with water (25 mL) and brine (25 mL), dried over Na$_2$SO$_4$ and evaporated to give the amidoxime (0.038 g, 35%). MS (ES+) 419, 420, 421.

Step 2: [6S/R,9R/S,11R/S]-2',3',4',5,5',6,7,9,10-Decahydro-2-(5-(4-fluorophenyl)-1,2,4-oxadiazol-3-yl)-5'-(2,2,2-trifluoroethyl)spiro[6,9-methanobenzocyclooctene-11,3'-[1,2,5]thiadiazole]1',1'-dioxide

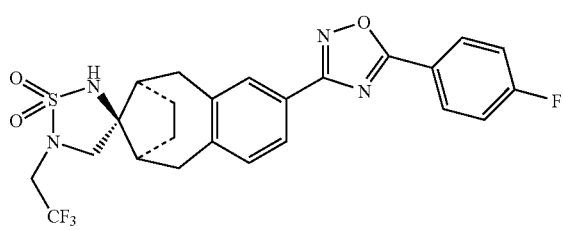

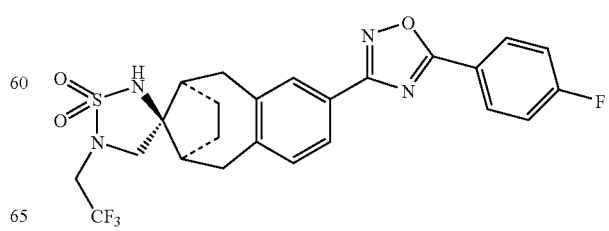

1,1'-Carbonyldiimidazole (0.032 g, 0.2 mmol) was added to a solution of 4-fluorobenzoic acid (0.028 g, 0.2 mmol) in N,N-dimethylformamide (3 mL) under nitrogen and stirred at room temperature for 1 hour. A solution of amidoxime (0.092 g, 0.22 mmol) in N,N-dimethylformamide (3 mL) was added and the reaction stirred at room temperature for 4 hours then at 70° C. for 5 hours. The cooled reaction mixture was diluted with ethyl acetate (25 mL) and washed with water (4×25 mL) and brine (25 mL), dried over $Na_2SO_4$ and evaporated. The residue (0.109 g) was dissolved in toluene (5 ml) and N,N-dimethylformamide (1 mL). p-Toluenesulphonic acid (3 mg) was added and the reaction heated under reflux for 5 hours. The cooled reaction mixture was poured into water (25 mL) and extracted with ethyl acetate (2×25 mL). The combined organic layers were washed with brine (25 mL), dried over $Na_2SO_4$ and evaporated. The residue was purified by flash column chromatography on silica, eluting with 25% ethyl acetate-isohexane to give the title compound (0.055 g, 48%). δ (1H, 400 MHz, $d_4$-MeOH) 1.22–1.30 (2H, m), 1.78–1.81 (2H, m), 2.48–2.53 (2H, m), 2.73–2.82 (2H, m), 3.39 (2H, dd, J=5, 16), 3.52 (2H, s), 3.88 (2H, q, J=9), 7.29 (1H, d, J=7.8), 7.34–7.40 (2H, m), 7.86–7.89 (2H, m), 8.26–8.30 (2H, m); MS (ES+) 523, 524, 526 ($[MH]^+$).

Example 2

[6S/R,9R/S,11R/S]2',3',4',5,5',6,7,8,9,10-Decahydro-2-(5-(2-pyridyl) -1,2,4-oxadiazol-3-yl)-5'-(2,2,2-trifluoroethyl)spiro[6,9-methanobenzocyclooctene-11,3'-[1,2,5]thiadiazole]1',1'-dioxide

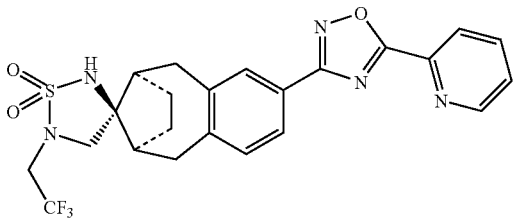

Prepared in the same way as Example 1 using 0.090 g of amidoxime from Step 1 and picolinic acid (0.024 g, 0.19 mmol) to give the title compound (0.046 g, 41%).
MS (ES+) 506, 507, 508.

Example 3

[6S,9R,11R]2',3',4',5,5',6,7,8,9,10-Decahydro-2-(5-(pyridin-2-yl)-1,2,4 -oxadiazol-3-yl)-5'-(2,2,2-trifluoroethyl)-spiro[6,9-methanobenzocyclooctene-11, 3'-[1,2,5]thiadiazole]1',1'-dioxide

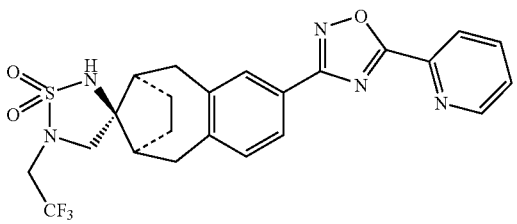

The racemic oxadiazole Example 2 was resolved by supercritical fluid chromatographic separation on a Chiralcel OD column using 30% methanol -sc-$CO_2$ as eluant (50 mL/min) at 35° C., 100 bar and UV detection at 250 nm, collecting the second compound eluted under these conditions.

Example 4

[6S/R,9R/S,11R/S]-2',3',4',5,5',6,7,8,9,10-Decahydro-2-(5-(3-pyridyl) -1,2,4-oxadiazol-3-yl)-5'-(2,2,2-trifluoroethyl)spiro[6,9-methanobenzocyclooctene-11,3'-[1,2,5]thiadiazole]1',1'-dioxide

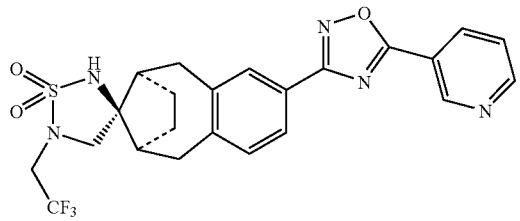

Prepared in the same way as Example 1 using 0.14 g of amidoxime from step 1 and nicotinic acid (0.037 g, 0.3 mmol) to give the title compound (0.027 g, 16%).
MS (ES+) 506, 507, 508, 547, 548

The invention claimed is:
1. A compound of formula I:

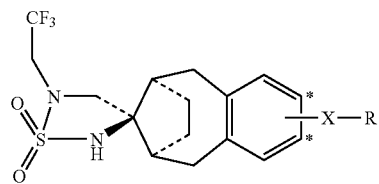

wherein the moiety X—R is attached at one of the positions indicated by an asterisk;
X is a 5-(R-substituted)-1,2,4-oxadiazol-3-yl moiety; and
R is selected from:
(i) a non-aromatic hydrocarbon group of up to 10 carbon atoms, optionally substituted with halogen, $CF_3$, $CHF_2$, CN, OH, $CO_2H$, $C_{2-6}$acyl, $C_{1-4}$alkoxy or $C_{1-4}$alkoxycarbonyl;
(ii) a non-aromatic heterocyclic group comprising up to 7 ring atoms of which up to 3 are chosen from N, O and S and the remainder are carbon, bearing 0–3 substituents independently selected from oxo, halogen, CN, $C_{1-6}$alkyl, OH, $CF_3$, $CHF_2$, $CH_2F$, $C_{2-6}$acyl, $CO_2H$, $C_{1-4}$ alkoxy and $C_{1-4}$alkoxycarbonyl; and
(iii) phenyl or 6-membered heteroaryl, either of which bears 0–3 substituents independently selected from halogen, $CF_3$, $CHF_2$, $CH_2F$, $NO_2$, CN, $OCF_3$, $C_{1-6}$alkyl and $C_{1-6}$alkoxy; or a pharmaceutically acceptable salt thereof.
2. A compound according to claim 1 which is homochiral and is [6S,9R,11R]2',3',4',5,5',6,7,8,9,10-decahydro-2-(5-(R-substituted)-1,2,4-oxadiazol -3yl)-5'-(2,2,2-trifluoroethyl)spiro[6,9-methanobenzocyclooctene-11,3'-[1,2,5]thiadiazole]1',1'-dioxide, or a pharmaceutically acceptable salt thereof.

3. A compound according to claim 1 or claim 2 wherein R represents phenyl or a 6-membered heteroaryl, either of which bears 0–3 substituents independently selected from halogen, $CF_3$, $CHF_2$, $CH_2F$, $NO_2$, CN, $OCF_3$, $C_{1-6}$alkyl and $C_{1-6}$alkoxy.

4. A compound according to claim 3 wherein R is selected from monohalophenyl, dihalophenyl, pyridyl, monohalopyridyl and trifluoromethylpyridyl, wherein "halo" refers to fluoro or chloro.

5. A compound according to claim 1 or claim 2 wherein the moiety —X—R is selected from:

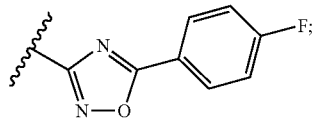

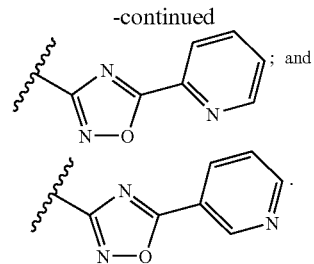

6. A pharmaceutical composition comprising a compound according to claim 1 and a pharmaceutically acceptable carrier.

7. A method of treatment of a subject suffering from or prone to Alzheimer's disease which comprises administering to that subject an effective amount of a compound according to claim 1.

* * * * *